(12) United States Patent
Bruno et al.

(10) Patent No.: US 12,558,361 B1
(45) Date of Patent: *Feb. 24, 2026

(54) METHOD AND COMPOSITION FOR TREATING NON-CIRRHOTIC NASH

(71) Applicant: Lipocine, Inc., Salt Lake City, UT (US)

(72) Inventors: Benjamin J. Bruno, Salt Lake City, UT (US); Nachiappan Chidambaram, Salt Lake City, UT (US); Kongnara Papangkorn, Salt Lake City, UT (US); Mahesh V Patel, Salt Lake City, UT (US); Kilyoung Kim, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/606,788

(22) Filed: Mar. 15, 2024

Related U.S. Application Data

(63) Continuation of application No. 17/573,592, filed on Jan. 11, 2022.

(60) Provisional application No. 63/136,185, filed on Jan. 11, 2021, provisional application No. 63/236,688, filed on Aug. 24, 2021.

(51) Int. Cl.
| | |
|---|---|
| *A61K 31/568* | (2006.01) |
| *A61K 31/355* | (2006.01) |
| *A61P 1/16* | (2006.01) |
| *G01N 33/68* | (2006.01) |

(52) U.S. Cl.
CPC .......... *A61K 31/568* (2013.01); *A61K 31/355* (2013.01); *A61P 1/16* (2018.01); *G01N 33/6893* (2013.01); *G01N 2800/085* (2013.01)

(58) Field of Classification Search
CPC ........ A61K 31/568; A61K 31/355; A61P 1/16
See application file for complete search history.

(56) References Cited

U.S. PATENT DOCUMENTS

| | | | |
|---|---|---|---|
| 2010/0173882 A1* | 7/2010 | Giliyar ................. | A61K 9/4875 514/178 |
| 2013/0225544 A1* | 8/2013 | Nachaegari .......... | A61K 9/4866 514/178 |

OTHER PUBLICATIONS

Jatenzo https://www.jatenzo.com/pdf/jatenzo-pi .pdf (Year: 2019).
Ozempic https://www.accessdata.fda.gov/drugsatfda_docs/label/2017/2096371bl.pdf.
Wegovy https://www.accessdata.fda.gov/drugsatfda_docs/label/2023/215256s0071bl.pdf.

* cited by examiner

*Primary Examiner* — San Ming R Hui
(74) *Attorney, Agent, or Firm* — Michael R. Schramm

(57) ABSTRACT

Disclosed is a method and composition for treating non-cirrhotic NASH. A first embodiment of the invention is the administration of a twice daily oral dose of approximately 117-400 mg testosterone equivalent to a subject having liver fibrosis. A second embodiment of the invention is the administration of a once or twice daily oral dose of approximately 117-400 mg testosterone equivalent formulated with approximately 200-600 mg of d-alpha tocopherol equivalent to a subject having liver fibrosis.

30 Claims, 5 Drawing Sheets

* p < 0.05;  p < 0.01; * p < 0.001 vs placebo

ALT (U/L) changes

Time (week)

* p < 0.05;  p < 0.01; * p < 0.001 vs placebo

* p < 0.05;  p < 0.01; * p < 0.001 vs placebo

METHOD AND COMPOSITION FOR TREATING NON-CIRRHOTIC NASH

CROSS REFERENCE TO RELATED APPLICATIONS

This nonprovisional utility patent application is a continuation of and claims the benefit under 35 USC § 120 to co-pending U.S. application Ser. No. 17/573,592 filed Jan. 11, 2022 which claims the benefit under 35 U.S.C. § 119(e) of U.S. provisional application Nos. 63/136,185, filed Jan. 11, 2021, and 63/236,688, filed Aug. 24, 2021, all of which are expressly incorporated herein, in their entirety, by this reference.

FIELD OF THE INVENTION

The present invention relates to compositions and methods for treating Non-Alcoholic Fatty Liver Disease (NAFLD) (see: the Wikipedia website for "NAFLD") and more especially for treating non-cirrhotic non-alcoholic steatohepatitis (NASH) (see: the Wikipedia website for "NASH"). The composition may be provided in oral and other dosage forms and the methods related to various associated methods of administration including particular dosing regimens. Accordingly, this invention involves the fields of chemistry, pharmaceutical sciences, medicine and other health sciences.

BACKGROUND OF THE INVENTION

Various methods of treatment and compositions therefor relating to various liver conditions are known in the art. Such methods and compositions are disclosed in the following list of US patent applications, all entitled "Liver Disease", and all of which are expressly incorporated herein in their entirety by this reference: 20200022991 entitled "Liver Disease" filed Aug. 28, 2019 and published Jan. 23, 2020, 20200155570 entitled "Liver Disease" filed Jul. 19, 2019 and published May 21, 2020, 2020038399 entitled "Liver Disease" filed Aug. 25, 2020 and published Dec. 10, 2020, 20200390785 entitled "Liver Disease" filed Aug. 25, 2020 and published Dec. 17, 2020, and 63/136,185 entitled "Method and Composition for Treating Non-Cirrhotic Nash" filed Jan. 11, 2021.

SUMMARY OF THE INVENTION

The present invention is a method and composition for treating NAFLD, and more especially for treating and/or preventing non-cirrhotic NASH. A first embodiment of the invention is the administration of a twice or once daily oral dose of approximately 117-400 mg testosterone equivalent to a subject having NAFLD. A second embodiment of the invention is the administration of a twice or once daily oral dose of approximately 117-400 mg testosterone equivalent formulated with approximately 200-600 mg (e.g. a range of 200-300 mg) of d-alpha oberol equivalent to a subject having NASH with liver fibrosis.

DETAILED DESCRIPTION OF THE INVENTION

Figure 1:
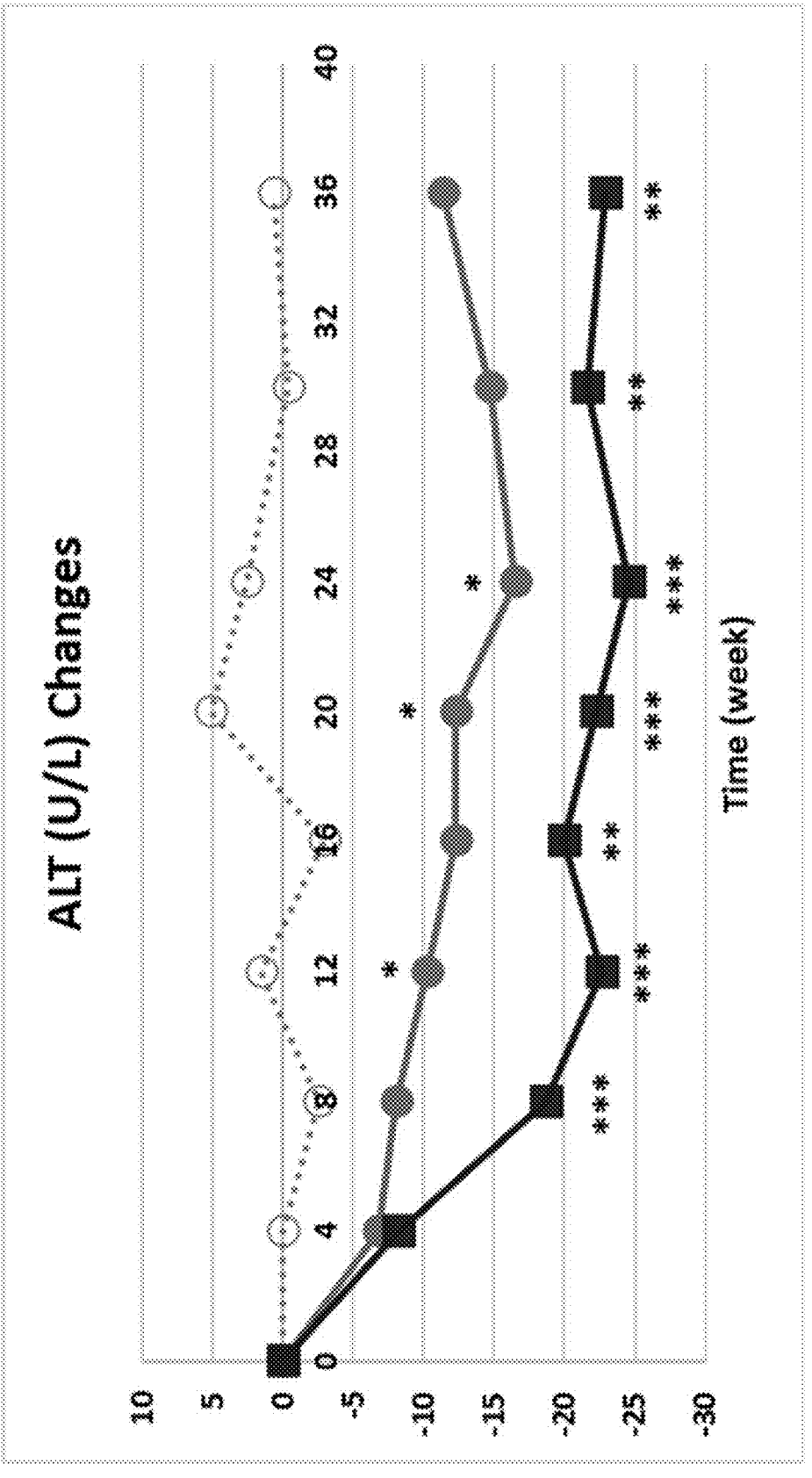
FIG. 1 shows changes in ALT as compared to a pretreatment baseline in exemplary results of a LIFT (Liver Fat Intervention with oral Testosterone) study.
Figure 2:
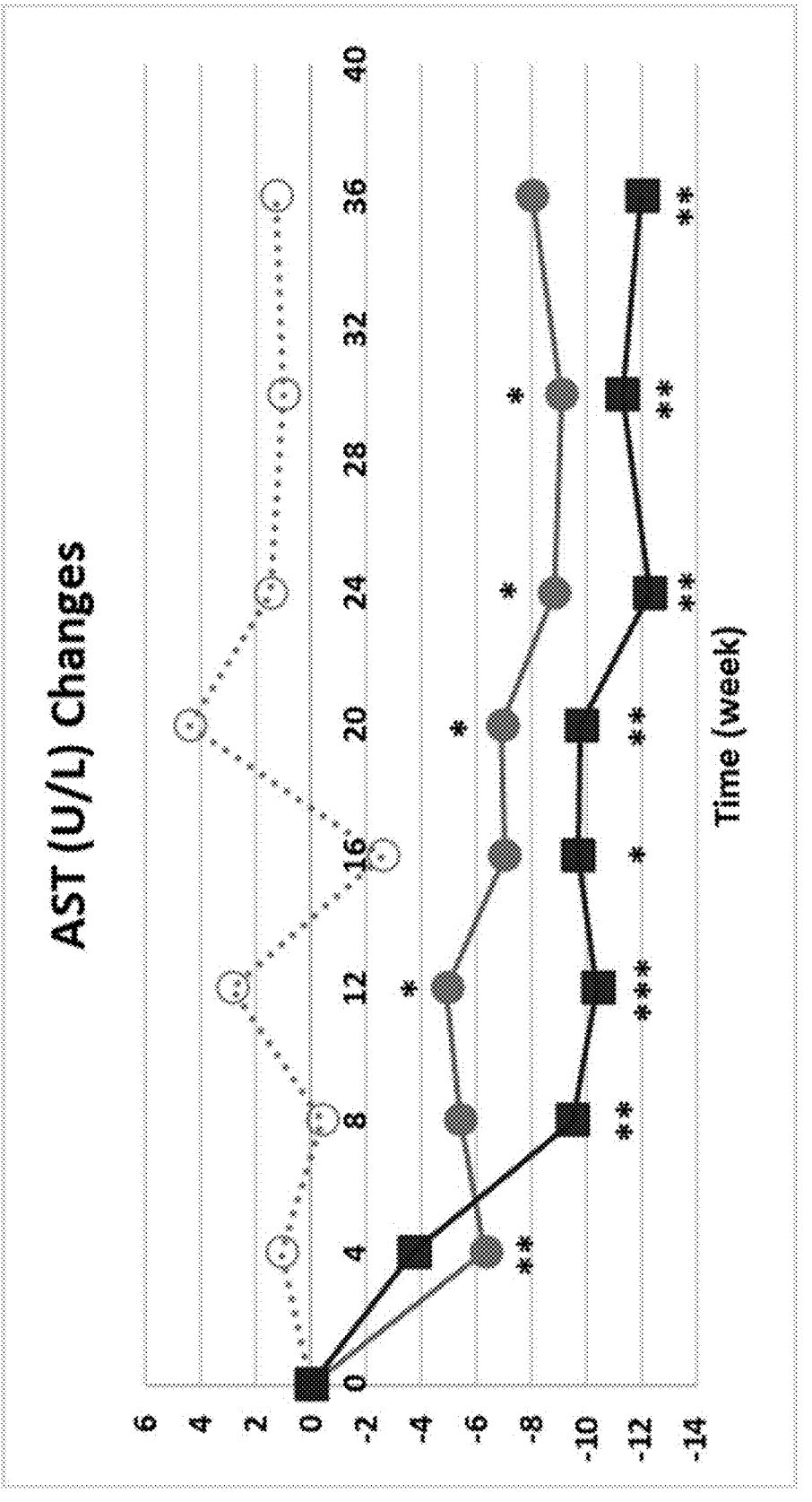
FIG. 2 shows changes in AST as compared to a pretreatment baseline in exemplary results of a LIFT study.
Figure 3:
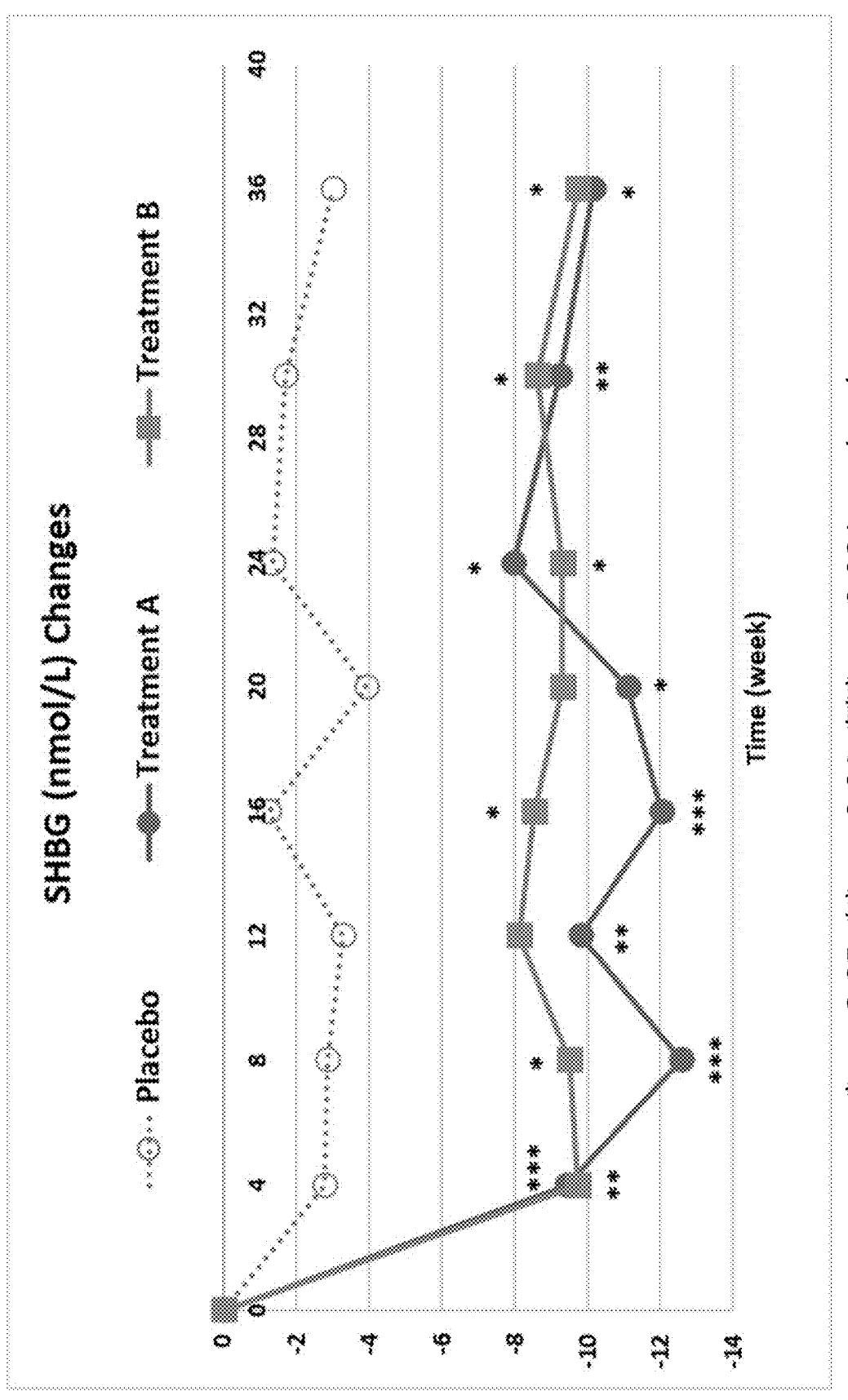
FIG. 3 shows changes in SHBG as compared to a pretreatment baseline in exemplary results of a LiFT study.
Figure 4:
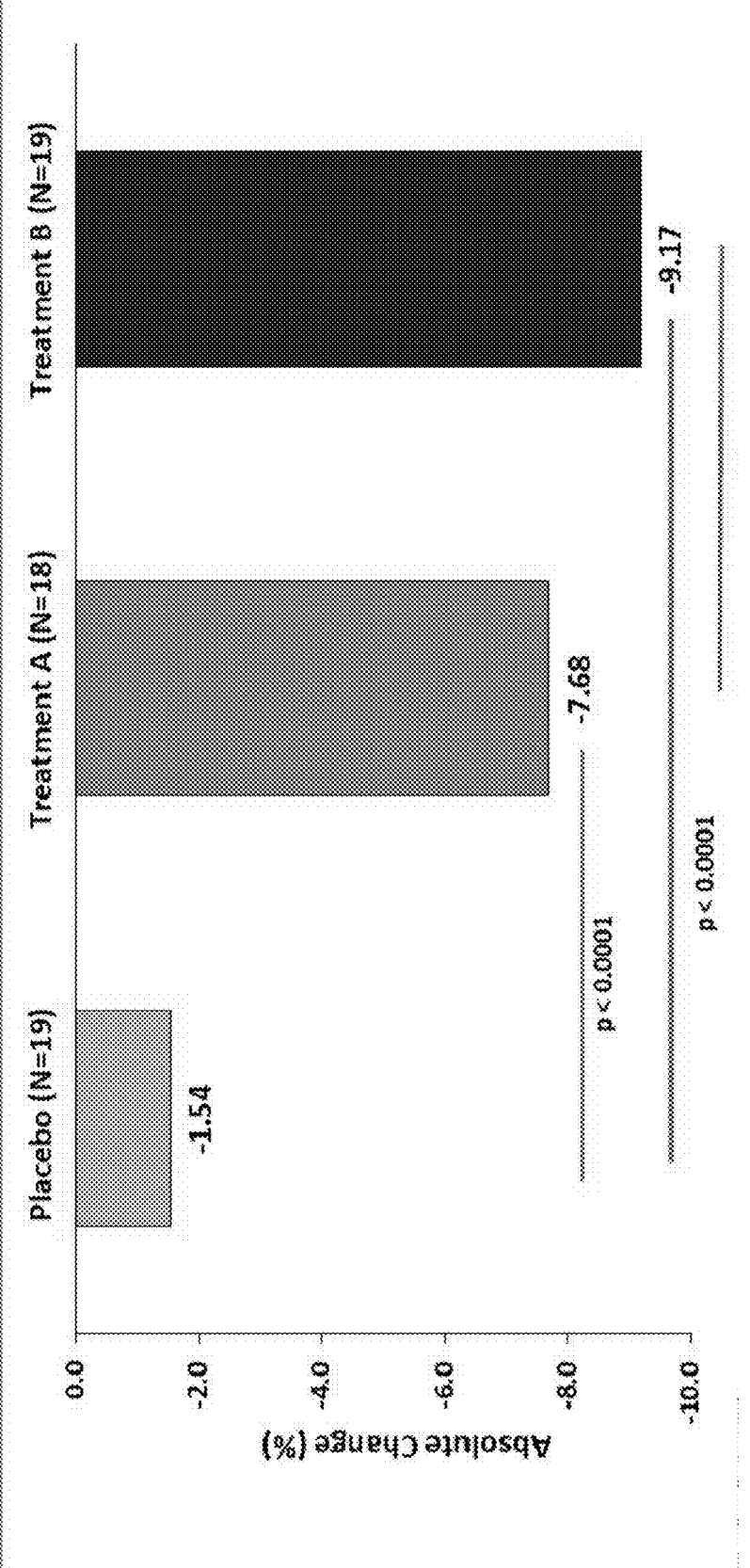
FIG. 4 shows changes in liver fat (LF) via MRI-PDFF in treatment groups as compared to the placebo group in exemplary results of a LiFT study.
Figure 5:
FIG. 5 shows the relative changes in appendicular lean mass and whole body fat mass in treatment groups as compared to the placebo group in exemplary results of a LIFT study.
Figure 5:
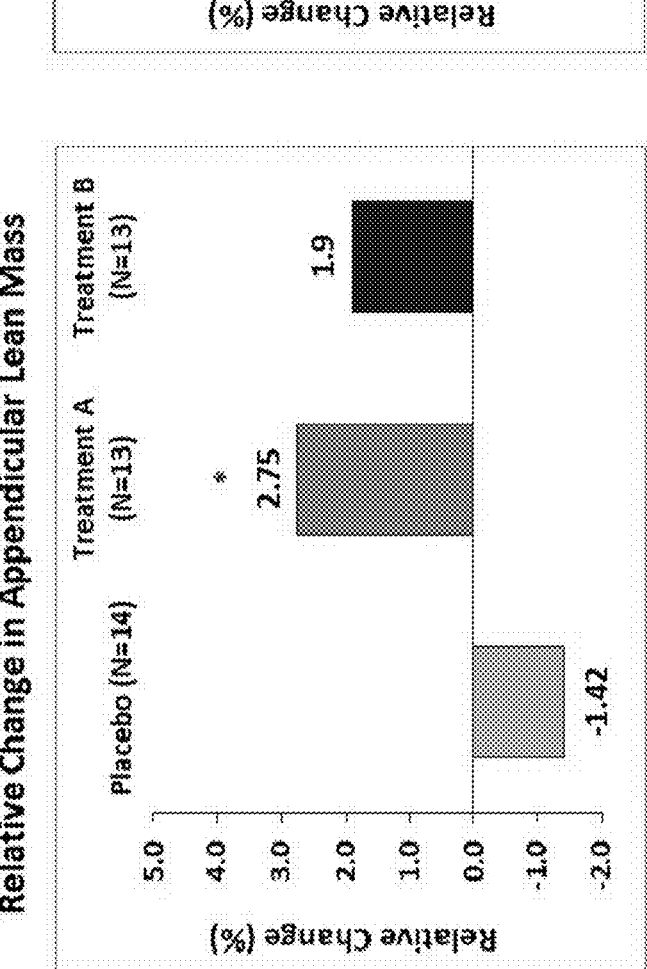

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

A first embodiment of the invention is the administration of a twice or once daily oral dose of approximately 117-400 mg testosterone equivalent to a subject having liver fibrosis. A second embodiment of the invention is the administration of a twice or once daily oral dose of approximately 117-400 mg testosterone equivalent formulated in the range of approximately 200-600 mg (for instance 238 mg) of d-alpha tocopherol equivalent to a subject having NASH with liver fibrosis.

Based on the doses, an amount for testosterone ester can be estimated for the T equivalent amount which is determined by the amount of testosterone per testosterone ester molecule. For example, for calculation purposes, 1.58 mg of T undecanoate is equivalent to 1 mg of T; 1.63 mg of T laurate is equivalent to 1 mg of T. That is, 1.58 is the conversion factor from T equivalent amount to T undecanoate amount, and 1.63 is the conversion factor from T equivalent amount to T laurate amount. Therefore, a skilled artisan understands how to estimate an amount of a testosterone ester for 'T equivalent amount' by dividing total amount of T ester by the conversion factor.

In one embodiment, a method of treatment comprising orally administering to a subject a pharmaceutical preparation comprising at least one of: a composition comprising testosterone ester (e.g. testosterone undecanoate (TU), testosterone duodecanoate (TD) or testosterone tridecanoate (TT)) in an amount sufficient to provide an equivalent amount of testosterone in said of 117-200 mg, and a composition comprising testosterone ester (e.g. testosterone undecanoate, testosterone duodecanoate or testosterone tridecanoate) in an amount sufficient to provide an equivalent amount of testosterone of 117-200 mg and d-alpha tocopherol or isomers thereof in a range of about 200-300 mg, wherein said pharmaceutical preparation is such that when administered to a group of subjects having biopsy confirmed NASH with fibrosis or suspected to have NASH with fibrosis or diagnosed with NASH with a noninvasive technique/methodology, relative to an equivalent placebo administration at least a predetermined percent of said subjects are responders (defined as subjects responding to the treatment attribute of interest) thereto, and wherein said NASH with fibrosis responder comprises a subject having at least one of: a NASH resolution comprising a lobular inflammation score of 0 or 1 and a hepatocyte ballooning score of 0 wherein the responder rate comprises at least about 30% of subjects based on NASH CRN scoring of the liver biopsy, a NASH resolution comprising a lobular inflammation score of 0 or 1, a hepatocyte ballooning score of 0, and no worsening of fibrosis wherein the responder rate comprises at least about 20% of subjects based on NASH CRN scoring of the liver biopsy, a NASH improvement based on NASH CRN scoring or paired read or digital read or a combination thereof, comprising improvement of hepatocyte ballooning or lobular inflammation and no worsening (no increase) of either hepatocyte ballooning or lobular inflammation wherein the responder rate comprises at least about 43% of subjects, a responder rate in hepatocyte ballooning decrease of at least 1 NASH CRN grade with at least about 34% of subjects, a responder rate in lobular inflammation decrease of at least 1 NASH CRN grade with at least about 30% of subjects, a responder rate in steatosis decrease of at least 1 NASH CRN grade with at least about 40% of subjects, a responder rate in improvement of fibrosis with at least about 10% of subjects, and a responder rate in improvement of fibrosis and no worsening of NASH with at least about 20% of subjects, an improvement in fibrosis and an improvement of NASH wherein the responder rate comprises at least about 33% of subjects, and a responder rate in improvement in fibrosis and a resolution of NASH wherein the responder rate comprises at least about 10% of subjects.

In another embodiment, the methods and composition of this invention is for a male subject, and wherein said NASH with fibrosis of said subjects of said group comprises a NASH with fibrosis stage of at least 2. In another embodiment, the method of this invention includes subject that has a NASH with fibrosis indication comprising at least one NASH with fibrosis biomarker (NFB) comprising: a predetermined ALT level, a predetermined AST level, a predetermined SHBG (Sex Hormone binding Globulin) level, a predetermined liver fat (LF) level, a predetermined histological steatosis (ST) NASH CRN grade, a predetermined histological liver cell ballooning (LCB) NASH CRN grade, a predetermined histological liver inflammation (LI) NASH CRN grade, a predetermined fibrosis NASH CRN stage, and a combination thereof. In one aspect, the method of this invention entails, in response to said administration, said at least one NFB of said subject is at least one of not worsened and improved, and wherein said improved NFB comprises at least one of: an ALT level decrease of at least about 13% compared to a pretreatment baseline of said subject prior to said administration of said pharmaceutical preparation, an AST level decrease of at least about 12% compared to a pretreatment baseline of said subject prior to said administration of said pharmaceutical preparation, a SHBG level decrease of at least about 23% compared to a pretreatment baseline of said subject prior to said administration of said pharmaceutical preparation, an LF level decrease of at least about 5% compared to a pretreatment baseline of said subject prior to said administration of said pharmaceutical preparation, an ST decrease in at least about 50% of subjects in a group of subjects compared to a pretreatment baseline of said subject prior to said administration of said pharmaceutical preparation, an LCB decrease in at least about 50% of subjects in a group of subjects compared to a pretreatment baseline of said subject prior to said administration of said pharmaceutical preparation, an LI decrease in at least about 40% of subjects in a group of subjects compared to a pretreatment baseline of said subject prior to said administration of said pharmaceutical preparation, and a combination thereof.

In another aspect, the said method includes the steps of: performing a biopsy-free non-invasive test (NIT) on said subject, said NIT comprising at least one of FIB-4, NFS, APRI, FIBROSURE, ELF, FIBROSCAN, MRE, MRI, MRI-PDFF, Proc3, and TNF alpha, performing digital pathology quantitative analysis on a specimen of said subject, and identifying said at least one NFB in said subject. In an additional aspect, the method comprising said pharmaceutical preparation is coadministered with at least one additional pharmaceutical preparation, and wherein administration of a single dose of said pharmaceutical preparation to said subject provides a total equivalent amount of testosterone to said subject in a range of about 117-400 mg, and wherein said pharmaceutical preparation is administered to said subject at least one of once daily and twice daily.

In one embodiment, the method entails response to said administration of said pharmaceutical preparation, body composition of said subject is improved, wherein said body composition improvement comprises at least one of a body weight maintenance, a body weight gain comprising a majority of muscle weight gain, a body weight loss comprising a majority of fat weight loss, an increase in bone density, and wherein said body weight gain comprises at least one of an appendicular lean muscle mass gain and a whole body lean mass gain, a whole body fat-free mass gain, and wherein said weight loss comprises a whole body fat mass loss, and wherein said body composition improvement is greater than a body composition improvement from a comparable administration of a placebo to said subject.

In one embodiment, a method of treatment comprising orally administering to a subject a pharmaceutical preparation, preferably a capsule dosage form, comprising at least one of: a composition comprising testosterone ester (e.g. testosterone undecanoate, duodecanoate or tridecanoate) in an amount sufficient to provide an equivalent amount of testosterone in said of 117-200 mg, and a composition comprising testosterone ester (e.g. testosterone undecanoate, duodecanoate or tridecanoate) in an amount sufficient to provide an equivalent amount of testosterone in said of 117-200 mg and d-alpha tocopherol in a range of about 200-300 mg, wherein said pharmaceutical preparation is such that when administered to a subject having at least one NASH with fibrosis indication, said at least one NASH with fibrosis indication is improved compared to a pretreatment baseline of said subject prior to said administration of said pharmaceutical preparation.

In another embodiment, the method of this invention for male subject having NASH with fibrosis or a group of subjects having a NASH with fibrosis stage of at least 2.

In one embodiment, pharmaceutical compositions and oral dosage units containing testosterone laurate and related methods comprise a dosing regimen to provide therapeutically effective levels of serum testosterone in male subjects having at least one of NASH, NASH with fibrosis, NASH with fibrosis of stage 2 or greater, fatty liver, hepatic fibrosis, and a combination thereof. In one aspect, the dosing regimen comprises an amount of testosterone equivalent from testosterone laurate ranging from 117 mg to 842 mg per day. In another aspect, the dosing regimen comprises an amount of an amount of testosterone equivalent from testosterone laurate of one of about 117 mg, about 125 mg, about 135 mg, about 145 mg, about 153 mg, about 165 mg, about 169 mg, about 184 mg, about 200 mg, about 225 mg, about 250 mg, about 275 mg, about 300 mg, about 320 mg, about 337 mg, about 350 mg, about 368 mg, about 380 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 824 mg, about 842 mg amount per day. In a further aspect, the corresponding dosing for female subjects is ¹/₁₀th-¹/₁₅th of the dosage values for male subjects in need of testosterone therapy for treating at least one of NASH, NASH with fibrosis, NASH with fibrosis of stage 2 or greater, fatty liver, hepatic fibrosis, and a combination thereof. In one embodiment, pharmaceutical compositions and oral dosage units containing testosterone laurate and related methods comprise a dosing regimen that administers pharmaceutical compositions and oral dosage units to subjects by one of once a day, twice a day, three times a day, and four times a day.

In one embodiment, pharmaceutical compositions and oral dosage units containing testosterone undecanoate and related methods comprise oral administration of 200 mg to 750 mg of testosterone undecanoate per day to a male subject in need of testosterone therapy for treating at least one of NASH, NASH with fibrosis, NASH with fibrosis of stage 2 or greater, fatty liver, hepatic fibrosis, and a combination thereof. In one aspect, said compositions and methods comprise oral administration of 300 mg to 600 mg of testosterone undecanoate per day to a male subject. In one aspect, said compositions and methods comprise oral administration of 400 mg to 600 mg of testosterone undecanoate per day to a male subject. In another aspect, said compositions and methods comprise oral administration of one of about 400 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, and about 590 mg, and about 600 mg of testosterone undecanoate per day to a male subject in need of testosterone therapy for treating at least one of NASH, NASH with fibrosis, NASH with fibrosis of stage 2 or greater, fatty liver, hepatic fibrosis, and a combination thereof. In a further aspect, the corresponding dosage is for female subjects is about ¹/₁₀th-¹/₁₅th of the dosage values for male subjects in need of testosterone therapy for treating at least one of NASH, NASH with fibrosis, NASH with fibrosis of stage 2 or greater, fatty liver, hepatic fibrosis, and a combination thereof. In one embodiment, pharmaceutical compositions and oral dosage units containing testosterone undecanoate and related methods comprise a dosing regimen that administers pharmaceutical compositions and oral dosage units to subjects by one of once a day, twice a day, three times a day, and four times a day.

In one embodiment, the methods and compositions herein can be used to treat biopsy or non-biopsy confirmed or suspected NASH patients with NASH disease or symptoms including any steatosis, inflammation, ballooning, fibrosis stage or type of NASH with fibrosis. In an aspect, the methods and compositions herein can provide liver biopsy based NASH resolution in a subject, which is defined as 0 grade of ballooning, 0 or 1 grade of inflammation, and any grade of steatosis according to the NASH Clinical Research Network (CRN) Classification. In another aspect, the methods and compositions herein can provide in a subject resolution of ballooning, which is defined as 0 grade or free of ballooning based on liver biopsy. In further aspect, the methods and compositions herein can provide in a subject NASH resolution without worsening of fibrosis based on liver biopsy. In yet another aspect, the methods and compositions herein can provide in a subject resolution of ballooning without worsening of fibrosis based on liver biopsy. In yet another aspect, the methods and compositions herein can provide in a subject resolution of ballooning and improvement of fibrosis based on liver biopsy. In another aspect, the methods and compositions herein can provide NASH resolution, which is defined as 0 grade of ballooning, 0 or 1 grade of inflammation, and any grade of steatosis according to the NASH Clinical Research Network (CRN) Classification based on liver biopsy in at least 10% of the NASH patients in a group after at least six months of treatment compared to patients NASH disease state prior start of the treatment.

In one embodiment, the diagnosis and evaluation of liver biopsies can be performed by typical reading techniques entailing a certified pathologist known in the prior art. For example, typical reading techniques (NASH CRN scoring, Paired read, digital read or combination thereof) used in the study of diagnosis and treatment including placebo to assess NASH resolution, or to assess no worsening of fibrosis, or to assess of NASH improvement, or to assess fibrosis improvement, or to assess no worsening of NASH, or to assess individual components of NASH such as steatosis, inflammation, ballooning, fibrosis using the present invention comprising compositions and methods are described as following:

NASH CRN Scoring: Screening biopsies were read as they became available (no tranches) to determine study eligibility for the current treatment. Post-treatment (End Of Study: EOS) reads were performed in tranches, with a mix of prior-treatment (baseline) and EOS biopsies in groups, to ensure the pathologist was blinded to timepoint and treatment group. Biopsies were scored for NASH components (steatosis, inflammation, and ballooning) as well as fibrosis using standard NASH CRN scoring. Change from pretreatment baseline in NAS components and fibrosis were generated by comparing the pretreatment baseline and EOS biopsy scores. NASH resolution, NASH worsening, fibrosis worsening and fibrosis improvement are defined per FDA's Phase 3 guidance or change in fibrosis stage.

Paired read: Pretreatment baseline and EOS biopsies were read as pairs (i.e., read side-by-side), with the condition that the pathologist was blinded to treatment group and timepoint. The screening and EOS biopsies were randomly assigned as 'Biopsy A' or 'Biopsy B'. The pathologist then scored each NASH component and fibrosis in Biopsy A as 'better, same, or worse' compared to Biopsy B. In this read technique, 'Improvement in NASH' or 'NASH improvement' is defined as an improvement in either inflammation and/or ballooning with no worsening (score of same or better) of both inflammation and ballooning and any score for steatosis. In this read technique, 'Improvement in fibrosis' or 'fibrosis improvement' is defined as a score of 'better' for fibrosis. In this technique, 'No worsening of NASH' is defined as a score of same or better of all NAS components (inflammation, ballooning, and steatosis).

Digital Read: Biopsy slides were digitized and analyzed using the FibroNest cloud-based image analysis tool (ref the website of FibroNest) while blinded to treatment group. Digital read technique using FibroNest tool reports a quantitative, continuous score for fibrosis severity for each biopsy. In this digital read, 'Fibrosis improvement' is defined as a decrease in the fibrosis composite score at EOS, post correcting for changes in steatosis (parenchymal tissue normalized phenotypic fibrosis composite score) compared to a pretreatment baseline.

In one aspect, the procedure of biopsy diagnosis and evaluation in a study with the current compositions and methods are given as following:

1) Subjects underwent a biopsy as part of the study screening procedures. This biopsy was sent to the central pathologist for processing and reading. The pathologist read the pretreatment baseline slides as they became available. If the subject met eligibility criteria, subject was invited to enroll in the study. At Week 36, the subject underwent a second biopsy, which was also sent to the central pathologist for processing. However, the EOS slide was not read immediately when it became available. Rather, EOS biopsies were read in tranches of 15 biopsy. 12 of the 15 were EOS biopsies, and 3 were pretreatment baseline biopsies. In this way, the pathologist remained blinded to the timepoint of the biopsy she was reading. Changes in NASH CRN scoring for NAS components and fibrosis stage were calculated by comparing the pretreatment baseline and EOS biopsy scores.

2) After an EOS slide was read in a tranche, the paired biopsy analysis was performed. As described above, the pathologist looked at a subject's two biopsies side-by-side. Central pathologist was unaware which of the two biopsies was the pretreatment baseline, and which was EOS. The pathologist then scored the biopsies as described above.

3) Once the paired read was completed, the trichome-stained slides (1 each from BL and EOS) were digitized and analyzed by FibroNest for fibrosis severity.

In yet another aspect, the methods and compositions herein can provide liver biopsy determined NASH resolution, which is defined as 0 grade of ballooning, 0 or 1 grade of inflammation, and any grade of liver biopsy determined steatosis according to the NASH Clinical Research Network (CRN) Classification in at least 10% of the NASH patients after at least six months of treatment compared to NASH patients on placebo. For an additional example, the methods and compositions herein can reduce NASH CRN grade of steatosis greater than or equal to one of 1, 2, and 3 grade as compared to the pretreatment baseline steatosis grade. Moreover, the methods and compositions herein can produce resolution of steatosis post treatment.

In one embodiment, the methods and compositions herein can reduce liver fat as measured via MRI-PDFF (Magnetic Resonance Imaging-Derived Proton Density Fat Fraction). For an example, the liver fat in a subject can be reduced by the current methods and compositions by as much as or greater than one of 1%, 2%, 3%, 4%, 5%, 6%, 7%, 8%, 9%, 10%, 11%, 12%, 13%, 14%, 15%, 16%, 17%, 18%, 19%, 20%, 23%, 25%, 27%, or 30% in absolute proportion. For another example, the liver fat can be reduced by the current methods and compositions by as much as or greater than one of 5%, 10%, 15%, 20%, 25% or 30% relative to the pretreatment baseline liver fat in a subject with fatty liver. The reduction of liver fat percentage can be determined by a % reduction in liver fat measured by MRI-PDFF. For yet further example, the fatty liver or liver fat can be reduced by the current methods and compositions by as much as or greater than one of 5%, 10%, 15%, 20%, 25%, 30%, 35%, 40%, 45%, or 50% relative to the placebo group.

In one embodiment, the methods and compositions disclosed herein can reduce levels of liver function markers, such as at least one of serum Alanine Aminotransfercase (ALT), Aspartate Aminotransferase (AST), Alkaline Phosphatase (ALP), gamma-glutamyl transferase (GGT), and bilirubin, as compared to pretreatment elevated serum liver function marker levels in subjects having at least one of NASH, NASH with fibrosis of stage 2 or greater, fatty liver, and hepatic fibrosis. In an aspect, the methods and compositions described herein can prevent worsening or improve or ameliorate liver function markers (e.g., ALT, AST, ALP, GGT, or bilirubin) by as much as or greater than one of 5%, 10%, 15%, 20%, 25%, 30%, 35%, 40%, 45%, and 50% as compared to pretreatment baseline levels. In another aspect, the methods and compositions described herein can prevent worsening, reduce, or ameliorate levels of liver function markers (e.g., ALT, AST, ALP, GGT) by as much as or greater than one of about 2 U/L, about 4 U/L, about 6 U/L, about 8 U/L, about 10 U/L, about 12 U/L, about 14 U/L, about 15 U/L, about 16 U/L, about 18 U/L, about 20 U/L, about 25 U/L, about 30 U/L, about 35 U/L, about 40 U/L, about 45 U/L, and about 50 U/L as compared to pretreatment baseline levels.

For evaluation of body composition improvement, Dual X-ray Absorptiometry scan (DXA) can be used to measure whole body lean mass (fat free mass), appendicular lean mass, whole body fat mass, and bone mineral density.

Whole body lean mass (or Whole body fat free mass): A component of body composition. Whole body lean mass or fat free mass can be calculated by subtracting body fat weight from total body weight: vice versa, total body weight is whole body lean mass plus whole body fat mass.

Appendicular lean muscle mass (ALMM): The sum of the lean tissue masses in the arms and legs. ALMM alone, or scaled to height squared (ALMM/height^2) or body mass index (ALMM/BMI) is the most common metric used as an approximation of muscle mass.

In one embodiment, the methods and compositions herein can be used to improve body compositions, which comprise whole body fat mass, whole body lean mass, and appendicular lean muscle mass measured by Dual Energy X-ray Absorptiometry (DXA). For an example, the whole body fat mass can be reduced by administering the oral compositions and methods described herein in a subject, having at least one of NASH, NASH with fibrosis of stage 2 or greater, fatty liver, and hepatic fibrosis, by as much as or greater than one of 0.1 kg, 0.2 kg, 0.3 kg, 0.4 kg, 0.5 kg, 0.6 kg, 0.7 kg, 0.8 kg, 0.9 kg, 1.0 kg, 1.2 kg, 1.4 kg, 1.5 kg, 1.6 kg, 1.8 kg, 2 kg, 2.5 kg, 3 kg, 4 kg, 5 kg, 6 kg, 7 kg, 8 kg, 9 kg, and 10 kg as compared to pretreatment baseline levels. For another example, the whole body fat mass can be reduced by administering the oral compositions and methods described herein to a subject, having at least one of NASH, NASH with fibrosis, NASH with fibrosis of stage 2 or greater, fatty liver, and fibrosis, greater than one of 0.5%, 1.0%, 1.5%, 2%, 2.5%, 3%, 3.5%, 4%, 4.5%, 5%, 6%, 7%, 8%, 9%, and 10% as compared to pretreatment whole body fat mass.

In one aspect, the whole body lean mass or fat free body mass can be increased by administering the oral compositions and methods described herein to a subject, having at least one of NASH, NASH with fibrosis of stage 2 or greater, fatty liver, and hepatic fibrosis, by as much as or greater than one of 0.1 kg, 0.2 kg, 0.3 kg, 0.4 kg, 0.5 kg, 0.6 kg, 0.7 kg, 0.8 kg, 0.9 kg, 1.0 kg, 1.2 kg, 1.4 kg, 1.5 kg, 1.6 kg, 1.8 kg, 2 kg, 2.5 kg, 3 kg, 4 kg, 5 kg, 6 kg, 7 kg, 8 kg, 9 kg, and 10 kg as compared to pretreatment baseline levels. In another aspect, the whole body lean mass or fat-free mass can be increased by administering the oral compositions and methods described herein to a subject, having at least one of NASH, NASH with fibrosis, NASH with fibrosis of stage 2 or greater, fatty liver, and fibrosis, greater than one of 0.5%, 1.0%, 1.5%, 2%, 2.5%, 3%, 3.5%, 4%, 4.5%, 5%, 6%, 7%, 8%, 9%, and 10% as compared to pretreatment whole body lean mass.

In further aspect, the appendicular lean muscle mass can be increased by administering the oral compositions and methods described herein to a subject, having at least one of NASH, NASH with fibrosis of stage 2 or greater, fatty liver, and hepatic fibrosis, by as much as or greater than one of 0.1 kg, 0.2 kg, 0.3 kg, 0.4 kg, 0.5 kg, 0.6 kg, 0.7 kg, 0.8 kg, 0.9 kg, 1.0 kg, 1.2 kg, 1.4 kg, 1.5 kg, 1.6 kg, 1.8 kg, 2 kg, 2.5 kg, 3 kg, 4 kg, 5 kg, 6 kg, 7 kg, 8 kg, 9 kg, and 10 kg as compared to pretreatment baseline levels. In another aspect, the appendicular lean muscle mass can be increased by administering the oral compositions and methods described herein to a subject, having at least one of NASH, fatty liver, and fibrosis, by as much as or greater than one of 0.5%, 1.0%, 1.5%, 2%, 2.5%, 3%, 3.5%, 4%, 4.5%, 5%, 6%, 7%, 8%, 9%, and 10% as compared to pretreatment appendicular lean muscle mass.

In one embodiment, the methods and compositions described herein can be used to treat at least one of NASH, NASH with fibrosis, NASH with fibrosis of stage 2 or greater, fatty liver, and hepatic fibrosis, to reduce a liver function marker (e.g., ALT, AST, ALP, GGT, bilirubin), and/or to improve body composition in a subject in need of treatment for at least one of NASH, NASH with fibrosis, NASH with fibrosis of stage 2 or greater, fatty liver, hepatic fibrosis, and a combination thereof.

In an aspect, the methods and compositions described herein can provide in a subject NASH resolution as graded via Clinical Research Network (CRN) Classification (i.e., 0 grade of ballooning, 0 or 1 grade of inflammation, and any grade of steatosis) and reduce a level of a liver function marker (e.g., ALT, AST, ALP, GGT, or bilirubin) as compared to pretreatment baseline levels. In another aspect, the methods and compositions described herein can improve in a subject body composition (e.g., whole body fat mass, whole body lean mass, and appendicular lean muscle mass) and reduce a level of a liver function marker (e.g., ALT, AST, ALP, GGT, or bilirubin) as compared to a pretreatment baseline level. In further aspect, the methods and compositions described herein can provide in a subject NASH resolution as graded via CRN Classification (i.e., 0 grade of ballooning, 0 or 1 grade of inflammation, and any grade of steatosis) and improve body compositions (e.g., whole body fat mass, whole body lean mass, and appendicular lean muscle mass). In yet another aspect, the methods and compositions described herein can provide in a subject NASH resolution as graded via CRN Classification (i.e., 0 grade of ballooning, 0 or 1 grade of inflammation, and any grade of steatosis) and reduce liver fat or the rate of increase in liver fat. In yet further aspect, the methods and compositions described herein can improve in a subject body composition (e.g., whole body fat mass, whole body lean mass, whole body fat-free mass, and appendicular lean muscle mass) and reduce liver fat. In yet further aspect, the methods and compositions described herein can reduce a level in a subject a liver function marker (e.g., ALT, AST, ALP, GGT, or bilirubin) as compared to pretreatment baseline levels and reduce liver fat.

In further aspect, the methods and compositions described herein can provide in a subject NASH resolution as graded via CRN Classification (i.e., 0 grade of ballooning, 0 or 1 grade of inflammation, and any grade of steatosis), improve body compositions (e.g., whole body fat mass, whole body lean mass, and appendicular lean muscle mass), and reduce liver fat as compared to pretreatment baseline levels. In further another aspect, the methods and compositions described herein can provide in a subject NASH resolution as graded via CRN Classification (i.e., 0 grade of ballooning, 0 or 1 grade of inflammation, and any grade of steatosis), improve body compositions (e.g., whole body fat mass, whole body lean mass, and appendicular lean muscle mass), and reduce levels of liver function markers (e.g., ALT, AST, ALP, GGT, or bilirubin) as compared to pretreatment baseline levels. In further another aspect, the methods and compositions described herein can provide in a subject NASH resolution as graded via CRN Classification (i.e., 0 grade of ballooning, 0 or 1 grade of inflammation, and any grade of steatosis), reduce liver fat, and reduce a level of a liver function marker (e.g., ALT, AST, ALP, GGT, or bilirubin) as compared to pretreatment baseline levels. In additional aspect, the methods and compositions described herein can reduce in a subject liver fat, improve body composition (e.g., whole body fat mass, whole body lean mass, whole body fat-free mass, and appendicular lean muscle mass), and a reduce level of a liver function marker (e.g., ALT, AST, ALP, GGT, or bilirubin) as compared to a pretreatment baseline level.

In yet further aspect, the methods and compositions described herein can provide in a subject NASH resolution as graded via CRN Classification (i.e., 0 grade of ballooning, 0 or 1 grade of inflammation, and any grade of steatosis), improve body composition (e.g., whole body fat mass, whole body lean mass, and appendicular lean muscle mass), reduce liver fat, and reduce a level of a liver function marker (e.g., ALT, AST, ALP, GGT, or bilirubin) as compared to a pretreatment baseline level.

In one embodiment, pharmaceutical compositions and oral dosage units containing testosterone laurate or testosterone undecanoate and related methods comprise oral administration of the oral dosage forms to treat at least one of NASH with fibrosis of stage2 or greater, fatty liver with fibrosis of at least 2 stage, and fibrosis only of stage 2 or greater, of which the grade can be 2, 3, or 4 stage according to the NASH Clinical Research Network (CRN) Classification.

In one embodiment, pharmaceutical compositions and oral dosage units containing testosterone laurate or testosterone undecanoate and related methods comprise oral administration of the oral dosage forms to subjects having at least one of NASH, NASH with fibrosis of stage 2 or greater, fatty liver, and hepatic fibrosis, who have endogenous testosterone levels (i.e., pretreatment serum testosterone levels) ranging from 1 ng/dl to 500 ng/dl. In one aspect, the compositions and methods can be used to treat NASH, NASH with Fibrosis of stage 2 or greater, fatty liver disease, and/or hepatic fibrosis in subjects who have a serum testosterone level of one of 1, 3, 5, 7, 10, 20, 30, 40, 50, about 75, about 100, about 150, about 200, about 250, about 300, about 350, about 400, about 450, and about 500 ng/dl as the subject's baseline (pretreatment) level (e.g., for a male subject or adjusted accordingly for female or pediatric subjects). In an aspect, the pretreatment baseline serum testosterone level can be determined by a single morning blood draw. Alternatively, the pretreatment baseline serum testosterone level can be determined by an average of two morning blood draws at similar time from different days.

In one embodiment, the pharmaceutical compositions and oral dosage units containing testosterone laurate or testosterone undecanoate and related methods can improve quality of life assessed by the Chronic Liver Disease Questionnaire (CLDQ), perceived Health-Related Quality of Life (HRQOL) score, depression measure, mobility measure, sexual dysfunction measure, Fatigue Impact Scale (FIS) questionnaire, Short Form-36 questionnaire (SF-36), and Psychosexual Domain Questionnaire (PDQ) in a subject having at least one of NASH, fatty liver, hepatic fibrosis, and NASH fibrosis ≥2 stage in need of treatment. In an aspect, oral compositions and methods of current invention can improve sexual symptoms including but not limited to sexual activity engagement, sexual thoughts or fantasies, feel of sexual desire, frequency of experience of morning erections, maintaining erections as long as desired, hardness of erection, ejaculation, and enjoyment/satisfaction of sexual activity. In addition, the sexual functions can be assessed by Psychosexual Daily Questionnaire (PDQ), which comprises 3 different domains representing 1) sexual desire, enjoyment, and performance; 2) sexual activity; and 3) mood. In another aspect, the oral compositions and the methods of current invention can improve or enhance the mental domain (e.g., mental component summary, mental health, role of emotion, social functioning), assessed by SF-36 (Short Form-36 Questionnaires).

In another aspect, pharmaceutical compositions and oral dosage units containing testosterone laurate or testosterone undecanoate and related methods can increase or enhance androgenic effects, such as hematocrit increase, hemoglobin increase, bone density, muscle mass, and etc.

In one embodiment, the pharmaceutical compositions and oral dosage units containing prodrugs of endogenous testosterone (e.g., testosterone laurate or testosterone undecanoate) and related methods can minimize adverse events typically observed with synthetic treatment candidates of NASH, NASH with fibrosis, NASH with fibrosis of stage 2 or greater, fatty liver, or hepatic fibrosis, such as obeticholic acid, FXR agonist, THR-b agonist, PPAR agonists, FGF agonist, GLP-1 agonist, CCR2 inhibitor, ACC inhibitor, ASK1 inhibitor, SCD-1 modulator, SGLT-2 inhibitor, and etc. For example, oral compositions and methods herein do not significantly increase frequency or severity of adverse events relative to placebo, such as at least one of hepatocellular carcinoma, drug induced liver injury (DILI), thromboembolic events, and/or sleep apnea. For another example, oral compositions and methods herein can have no significant adverse changes in at least one of total cholesterol, triglyceride, and LDL levels as compared to pretreatment baseline levels or placebo. Moreover, the oral compositions and methods herein can produce treatment that results in less than 10% frequency in a group and up to moderate severity of gastrointestinal tract related adverse events, which include diarrhea, nausea, vomiting, abdominal pain, headache, dizziness, constipation, and etc.

In an aspect, adverse events related to gastrointestinal tract in the treated groups, who are treated with pharmaceutical compositions and oral dosage units containing testosterone laurate or testosterone undecanoate and related methods, are comparable to placebo group.

In further aspect, pharmaceutical compositions and oral dosage units containing testosterone laurate or testosterone undecanoate and related methods do not clinically meaningfully increase cardiovascular risk in patients in need of a treatment who have at least one of NASH, NASH with fibrosis, NASH with Fibrosis of stage 2 or greater, fatty liver, and hepatic fibrosis.

Additional disclosure of the present invention is provided in Appendices A, B and C of U.S. provisional application Nos. 63/136,185 and 63/236,688 which are incorporated by reference in this application.

The API in this example in specific compositions is testosterone tridecanoate, testosterone undecanoate, or a combination thereof. Alternatively, the skilled artisan understands that any other testosterone ester or steroid, or steroid ester can be used in these compositions accordingly.

| Composition (D) | | | |
|---|---|---|---|
| | Quantity Fill Material per Hard Gel Capsule | | Quantity Fill Material Softgel Capsule |
| Ingredient Name | % w/w | mg | mg |
| API | 25%-32% | 160-205 | 304-390 |
| Oleic Acid, NF ((9Z)-Octadec-9-enoic acid) | 50%-60% | 340-400 | 646-760 |
| Polyoxyl 40 Hydrogenated Castor Oil, NF | 0%-7% | 21-32 | 0-61 |
| Stearic Acid, NF | 0%-7% | 0-32 | 0-61 |
| Glyceryl Palmitostearate (Glyceryl Distearate, NF; Precirol ATO 5) | 3%-13% | 47-58 | 89-110 |
| Ascorbyl Palmitate, NF | 0.1%-3% | 0.5-2.5 | 1.0-4.8 |
| Total | 100.00 | 654.60 | 1250 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oral dosage form pharmaceutical composition for use in improving body composition from at least one of fat mass reduction without attendant non-fat mass reduction and fat mass reduction with attendant non-fat mass increase, said composition comprising at least one testosterone ester component (TEC) and greater than 15% w/w of a lipophilic additive, wherein said TEC consists essentially of a combination of at least one of TU and TT, and TD and TT, and wherein an amount and ratio of said TEC and said lipophilic additive are such that administration of said composition to a subject having a minimum BMI results in an improvement in body composition comprising a body weight loss from at least one of a fat mass reduction without attendant non-fat mass loss, and a fat mass reduction with attendant non-fat mass increase, and wherein said minimum BMI comprises at least one of 25, 27, and 30, and wherein said fat mass reduction without attendant non-fat mass loss comprises a minimum w/w fat mass reduction of at least one of 5%, 6%, 7%, 8%, 9%, and 10%, and wherein said fat mass reduction with attendant non-fat mass increase comprises a minimum w/w fat mass reduction of at least one of 5%, 6%, 7%, 8%, 9%, and 10%.

2. The composition of claim 1, wherein said fat mass reduction with attendant non-fat mass increase comprises a minimum w/w non-fat mass increase of at least one of 2%, 3%, 4%, 5%, 6%, and 7%.

3. The composition of claim 1, wherein said fat mass reduction comprises at least one of whole body fat mass reduction and appendicular fat mass reduction, and wherein when said fat mass reduction comprises whole body fat mass reduction, said minimum w/w fat mass reduction comprises whole body fat mass reduction, and wherein when said fat mass reduction comprises appendicular fat mass reduction, said minimum w/w fat mass reduction comprises appendicular fat mass reduction.

4. The composition of claim 1, wherein an amount and ratio of said testosterone ester and said tocopherol are such that said administration results in an increase in at least one ratio comprising a whole body non-fat mass to total whole body fat mass ratio (Body Ratio or BR) and an appendicular non-fat mass to appendicular fat mass ratio (Appendicular Ratio or AR).

5. The composition of claim 4, wherein said increase of said BR comprises a minimum increase of at least one of 2%, 4%, 6%, 8%, 10%, and 12%, and wherein said increase of said AR comprises a minimum increase of at least one of 2%, 4%, 6%, 8%, 10%, and 12%.

6. The composition of claim 1, wherein said administration comprises at least one of a once daily administration and a twice daily administration, and wherein said lipophilic additive comprises at least one of d-alpha tocopherol and an equivalent of d-alpha tocopherol (DAT).

7. The composition of claim 1, wherein said amount and ratio of said TEC and said lipophilic additive comprises said TEC in an amount sufficient to provide an equivalent amount of testosterone in said subject of 117-200 mg and a DAT in a range of about 200-300 mg.

8. The composition of claim 1, wherein when said subject is female, a dosage of said composition administered to said female subject is about 10% to about 15% as much as a dosage of said composition administered to a male subject.

9. The composition of claim 1, wherein said composition comprises said TEC in about 25% to 32% w/w of said composition and said lipophilic additive comprises a DAT in about 20% to 85% w/w of said composition.

10. The composition of claim 1, wherein said composition comprises a plurality of excipients, said excipients comprising a fatty acid in a w/w % of said composition of at least double the amount of said TEC and a Polyoxyl 40 Hydrogenated Castor Oil in a w/w % of said composition of no more than half the amount of said TEC.

11. The composition of claim 1, wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor.

12. The composition of claim 1, wherein said composition comprises said TEC in an amount sufficient to provide an equivalent amount of testosterone in said subject of 117-200 mg and said lipophilic additive comprises a DAT in a range of about 200-300 mg, and wherein said minimum BMI comprises 27, and wherein said composition comprises a plurality of excipients, said excipients comprising a fatty acid in a w/w % of said composition of at least double the amount of said TEC and a Polyoxyl 40 Hydrogenated Castor Oil in a w/w % of said composition of no more than half the amount of said TEC, and wherein said administration comprises at least one of a once daily administration and a twice daily administration, and wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor, and wherein said administration results in a minimum w/w whole body fat mass reduction of at least 3% and attendant minimum w/w whole body non-fat mass increase of 0% to 1%.

13. An oral dosage form pharmaceutical composition for use in improving body composition from at least one of fat mass reduction without attendant non-fat mass reduction and fat mass reduction with attendant non-fat mass increase, said composition comprising at least one TEC and greater than 15% w/w of a lipophilic additive, wherein said TEC consists essentially of a combination of at least one TU and TT, and TD and TT, and wherein an amount and ratio of said TEC and said lipophilic additive are such that administration of said composition to a subject having a minimum BMI results in an improvement in body composition comprising a body weight loss from an increase in at least one of a BR and an AR, and wherein said minimum BMI comprises at least one of 25, 27, and 30, and wherein said increase of said BR comprises a minimum increase of at least one of 2%, 4%, 6%, 8%, 10%, and 12%, and wherein said increase of said AR comprises a minimum increase of at least one of 2%, 4%, 6%, 8%, 10%, and 12%.

14. The composition of claim 13, wherein an amount and ratio of said TEC and said lipophilic additive are such that administration of said composition to a subject results in at least one of a fat mass reduction without attendant non-fat mass loss, and a fat mass reduction with attendant non-fat mass increase, and wherein said fat mass reduction without attendant non-fat mass loss comprises a minimum w/w fat mass reduction of at least one of 5%, 6%, 7%, 8%, 9%, and 10%, and wherein said fat mass reduction with attendant non-fat mass increase comprises a minimum w/w fat mass reduction of at least one of 5%, 6%, 7%, 8%, 9%, and 10%.

15. The composition of claim 14, wherein said fat mass reduction with attendant non-fat mass increase comprises a minimum w/w non-fat mass increase of at least one of 2%, 3%, 4%, 5%, 6%, and 7%.

16. The composition of claim 14, wherein said fat mass reduction comprises at least one of whole body fat mass reduction and appendicular fat mass reduction, and wherein when said fat mass reduction comprises whole body fat mass reduction, said minimum w/w fat mass reduction comprises whole body fat mass reduction, and wherein when said fat mass reduction comprises appendicular fat mass reduction, said minimum w/w fat mass reduction comprises appendicular fat mass reduction.

17. The composition of claim 13, wherein said administration comprises at least one of a once daily administration and a twice daily administration, and wherein said lipophilic additive comprises at least one of a DAT.

18. The composition of claim 13, wherein said amount and ratio of said TEC and said lipophilic additive comprises said TEC in an amount sufficient to provide an equivalent amount of testosterone in said subject of 117-200 mg and a DAT in a range of about 200-300 mg.

19. The composition of claim 13, wherein when said subject is female, a dosage of said composition administered to said female subject is about 10% to about 15% as much as a dosage of said composition administered to a male subject.

20. The composition of claim 13, wherein said composition comprises said TEC in about 25% to 32% w/w of said composition and said lipophilic additive comprises a DAT in about 20% to 85% w/w of said composition.

21. The composition of claim 13, wherein said composition comprises a plurality of excipients, said excipients comprising a fatty acid in a w/w % of said composition of at least double the amount of said TEC and a Polyoxyl 40 Hydrogenated Castor Oil in a w/w % of said composition of no more than half the amount of said TEC.

22. The composition of claim 13, wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor.

23. The composition of claim 13, wherein said composition comprises said TEC in an amount sufficient to provide an equivalent amount of testosterone in said subject of 117-200 mg and a DAT in a range of about 200-300 mg, and
   wherein said minimum BMI comprises 27, and
   wherein said composition comprises a plurality of excipients, said excipients comprising a fatty acid in a w/w % of said composition of at least double the amount of said TEC and a Polyoxyl 40 Hydrogenated Castor Oil in a w/w % of said composition of no more than half the amount of said TEC, and
   wherein said administration comprises at least one of a once daily administration and a twice daily administration, and
   wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor, and
   wherein said administration results in a minimum w/w whole body fat mass reduction of at least 3% and attendant minimum w/w whole body non-fat mass increase of 0% to 1%.

24. A method for use in improving body composition from at least one of fat mass reduction without attendant non-fat mass reduction and fat mass reduction with attendant non-fat mass increase, said method comprising orally administering to a subject the oral dosage form pharmaceutical composition of claim 1.

25. The method of claim 24, wherein said amount and ratio of said TEC and said lipophilic additive comprises said TEC in an amount sufficient to provide an equivalent amount of testosterone in said subject of 117-200 mg and said lipophilic additive comprises a DAT in a range of about 200-300 mg.

26. The method of claim 24, wherein said lipophilic additive comprises a DAT, and
   wherein said minimum BMI comprises 27, and
   wherein when said subject is female, a dosage of said composition administered to said female subject is about 10% to about 15% as much as a dosage of said composition administered to a male subject, and
   wherein said composition comprises at least one of said TEC in about 25% to 32% w/w of said composition and said DAT in about 20% to 85% w/w of said composition.

27. The method of claim 24, wherein said composition comprises a plurality of excipients, said excipients comprising a fatty acid in a w/w % of said composition of at least double the amount of said TEC and a Polyoxyl 40 Hydrogenated Castor Oil in a w/w % of said composition of no more than half the amount of said TEC.

28. The method of claim 24, wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor.

29. An oral dosage form pharmaceutical composition for use in improving body composition from at least one of fat mass reduction without attendant non-fat mass reduction and fat mass reduction with attendant non-fat mass increase, said composition comprising:
   a TEC consisting essentially of a combination of at least one of TU and TT, and TD and TT and being in an amount sufficient to provide an equivalent amount of testosterone in said subject of 117-200 mg and to comprise at least 25% w/w of said composition,
   a lipophilic additive in a range of about 200-300 mg and comprising greater than 15% w/w of said composition,
   and a plurality of excipients wherein said excipients comprise a fatty acid in a w/w % of said composition of at least double said amount of said TEC and a Polyoxyl 40 Hydrogenated Castor Oil in a w/w % of said composition of no more than half said amount of said TEC,
   wherein said amount and ratio of said TEC and said lipophilic additive are such that administration of said composition to a subject having a minimum BMI of 27 results in an improvement in body composition comprising a body weight loss from at least one of a fat mass reduction without attendant non-fat mass loss, and a fat mass reduction with attendant non-fat mass increase, and
   wherein said fat mass reduction without attendant non-fat mass loss comprises a minimum w/w fat mass reduction of at least one of 5%, 6%, 7%, 8%, 9%, and 10%, and
   wherein said fat mass reduction with attendant non-fat mass increase comprises a minimum w/w fat mass reduction of at least one of 5%, 6%, 7%, 8%, 9%, and 10%.

30. The composition of claim 29, wherein said administration comprises a coadministration of said composition and at least one of obeticholic acid, an FXR agonist, a THR-b agonist, a PPAR agonists, an FGF agonist, a GLP-1 agonist, a CCR2 inhibitor, an ACC inhibitor, an ASK1 inhibitor, an SCD-1 modulator, and an SGLT-2 inhibitor.

* * * * *